(12) United States Patent
Cowan et al.

(10) Patent No.: US 7,751,881 B2
(45) Date of Patent: Jul. 6, 2010

(54) ACOUSTICALLY-POWERED WIRELESS DEFIBRILLATOR

(75) Inventors: Mark W. Cowan, Fremont, CA (US); Axel F. Brisken, Fremont, CA (US)

(73) Assignee: EBR Systems, Inc., Sunnyvale, CA (US)

(*) Notice: Subject to any disclaimer, the term of this patent is extended or adjusted under 35 U.S.C. 154(b) by 0 days.

(21) Appl. No.: 11/764,546

(22) Filed: Jun. 18, 2007

(65) Prior Publication Data

US 2007/0293895 A1 Dec. 20, 2007

Related U.S. Application Data

(60) Provisional application No. 60/805,312, filed on Jun. 20, 2006.

(51) Int. Cl.
*A61N 1/00* (2006.01)
(52) U.S. Cl. .......................................................... 607/5
(58) Field of Classification Search .............. 607/4, 607/5, 9, 10, 30, 32, 33, 35, 60, 61
See application file for complete search history.

(56) References Cited

U.S. PATENT DOCUMENTS

| | | | |
|---|---|---|---|
| 5,411,535 A * | 5/1995 | Fujii et al. | 607/32 |
| 5,749,909 A | 5/1998 | Schroeppel et al. | |
| 6,266,567 B1 | 7/2001 | Ishikawa et al. | |
| 6,315,721 B2 | 11/2001 | Schulman et al. | |
| 6,640,135 B1 * | 10/2003 | Salo et al. | 607/9 |
| 6,647,292 B1 | 11/2003 | Bardy et al. | |
| 6,721,597 B1 | 4/2004 | Bardy et al. | |
| 2002/0042630 A1 * | 4/2002 | Bardy et al. | 607/5 |
| 2002/0103523 A1 * | 8/2002 | Helland et al. | 607/122 |
| 2002/0183791 A1 | 12/2002 | Denker et al. | |
| 2004/0172083 A1 * | 9/2004 | Penner | 607/35 |
| 2005/0038474 A1 | 2/2005 | Wool | |
| 2006/0136004 A1 | 6/2006 | Cowan et al. | |
| 2006/0136005 A1 | 6/2006 | Brisken et al. | |

OTHER PUBLICATIONS

Duffin et al., "Implantable Cardioverter-Defibrillator: An Overview and Future Direction," Singer, Igor (editor), *Implantable Cardioverter-Defibrillator*, Futura Publishing Co., Inc., New York, 1994, Chapter 36, 751-767.
International Search Report and Written Opinion of PCT Application No. PCT/US07/71687, mailed Oct. 10, 2008, 9 pages.

* cited by examiner

*Primary Examiner*—Mark W Bockelman
*Assistant Examiner*—Roland Dinga
(74) *Attorney, Agent, or Firm*—Townsend and Townsend and Crew LLP (57) ABSTRACT

An acoustic transmitter produces a pulsed ultrasound waveform which is transmitted through body tissues to an implanted receiver-stimulator device. The waveform has an acoustic amplitude, pulse width, and pulse repetition period, which corresponds to a pacing pulse electrical amplitude, pacing pulse width, and pacing cycle length, respectively. The receiver-stimulator device intercepts at least a portion of the transmitted acoustic energy and coverts that acoustic energy into electrical energy using piezoelectric or other devices. This electrical energy is applied to circuitry, which produces a desired stimulating pulse waveform, which is then applied to tissue-contacting electrodes.

29 Claims, 5 Drawing Sheets

ACOUSTICALLY-POWERED WIRELESS DEFIBRILLATOR

CROSS-REFERENCES TO RELATED APPLICATIONS

The present application claims the benefit of provisional U.S. Application No. 60/805,312, filed Jun. 20, 2006, the full disclosure of which is incorporated herein by reference.

BACKGROUND OF THE INVENTION

1. Field of the Invention

This invention relates to implantable devices used to defibrillate and pace the heart and more specifically to systems and methods for providing such defibrillation and pacing that transmit energy acoustically from an implanted transmitter to an implanted receiver without the use of conventional lead/electrode systems.

Currently available implantable cardioverter-defibrillator (ICD) devices apply an electrical defibrillation shock to the heart through a lead wire having an electrode, such lead wire and electrode typically being placed within the right ventricle of the heart, and with the shock typically being delivered between this first electrode and the posterior side of the implanted ICD pulse generator housing, which acts as a second electrode. Alternatively, the shock may be delivered between two electrodes on the lead wire, or between the two electrodes and the ICD pulse generator. Current ICD devices also deliver both bradycardia pacing and tachycardia pacing via a bipolar electrode pair located at the distal end of the lead wire in the right ventricle. The lead wires used in pacemakers and ICDs are subject to failure and may cause cardiac perforation, thrombo-occlusion, and infections. Several years after lead implantation, lead failure, due to fracture or insulation break, has been reported to occur in a significant fraction of the patient population.

An ICD-type device currently under development does not require intracardiac lead wires (Cameron Health, Inc., San Clemente, Calif.). Instead of implanting leads in the heart, the device is implanted under the skin of the patient in the left chest area, with one electrode incorporated into the outer body of the implanted device and a second electrode disposed on a subcutaneous lead. These electrodes are situated to deliver the defibrillation energy approximately across the heart, through the chest wall in a fashion similar to a conventional external defibrillator.

Typically, an ICD delivers a shock with a total energy of 3 to 35 Joules, where the leadless subcutaneous device under development is reported to deliver a shock of more than 35 Joules. In either case, due to the location of one or more electrodes (the pulse generator case for a conventional leaded ICD, or the multiple electrodes outside of the chest wall for the subcutaneous device) being located within or close to the musculature of the chest, the delivery of the shock results in skeletal muscle contraction. This can be extremely painful for the patient. While this may not be a concern in the case of ventricular fibrillation as the patient is typically unconscious, ICDs are also programmed to provide shocks to terminate ventricular tachycardia, where the patient is, typically, fully conscious. In fact, the majority of shocks delivered by such ICDs are for the conversion of ventricular tachycardia, before it degenerates into ventricular fibrillation. Furthermore, it would be desirable to utilize ICD-type devices to terminate atrial fibrillation, a condition which is not immediately life threatening, but is associated with increased morbidity and is an uncomfortable condition for most patients. The pain associated with the shock delivery of present ICDs has essentially precluded their use to treat this condition.

Another potentially serious drawback of conventional ICD technology is the latency between the detection of an arrhythmia and the ability to deliver a defibrillation shock. This time-lag is associated with the charging of a large storage capacitor from a current-limited battery, and is typically over 5 seconds with a fully charged battery, and can be 10 to 12 seconds with a device nearing the end of its battery life. Such a long time lag between the detection and defibrillation could be the source of serious, and some times fatal, consequences.

Thus, because of the known problems associated with the use of lead wires, it would be desirable to eliminate the requirement for these lead wire/electrode systems used in present ICDs. Further, it would be desirable to provide shock-based treatment for ventricular and atrial fibrillation, and ventricular tachycardia, with less pain associated with shock delivery, and by providing that treatment internal to the heart without requiring transmission of the shock energy through the musculature of the chest. Additionally, it would be desirable to provide the defibrillation or cardioversion therapy with less latency between the detection of an arrhythmia and the application of the shock.

2. Description of the Background Art

References: U.S. Pat. No. 6,266,567, Ishikawa et al., Implantable Epicardial Electrode, Jul. 24, 2001; U.S. Patent Application Publication US2002/0183791A1, Denker et al., Implantable Defibrillator with Wireless Vascular Stent Electrodes; U.S. Pat. No. 6,647,292, Bardy et al., Unitary Subcutaneous Only Implantable Cardioverter-Defibrillator and Optional Pacer, Nov. 11, 2003; U.S. Pat. No. 6,721,597, Bardy et al., Subcutaneous Only Implantable Cardioverter-Defibrillator and Optional Pacer, Apr. 13, 2004; U.S. Patent Application Publication US2005/0038474A1, Wool, Implantable Automatic Defibrillator with Subcutaneous Electrodes, Feb. 17, 2005; Singer, Igor (editor), Implantable Cardioverter-Defibrillator, Futura Publishing Co., Inc., New York, 1994.

BRIEF SUMMARY OF THE INVENTION

Wireless acoustic pacemaker and tissue stimulation methods and systems have previously been described in co-pending application Ser. No. 11/315,023 (Attorney Docket No. 021834-000820US), filed on Dec. 21, 2005; and Ser. No. 11/315,524 (Attorney Docket No. 021834-001010US), filed on Dec. 21, 2005 and these applications are incorporated in this disclosure in their entirety. In the systems described in these applications, a subcutaneously implanted or external acoustic transmitter produces a pulsed ultrasound waveform, which is transmitted through body tissues to an implanted receiver-stimulator device. The transmitted ultrasonic waveform has an acoustic amplitude, pulse width, and pulse repetition period, which in a conventional pacemaker system would correspond to the pacing pulse electrical amplitude, pacing pulse width, and pacing cycle length, respectively. The receiver-stimulator device intercepts at least a portion of the transmitted acoustic energy, and converts that acoustic energy into electrical energy using piezoelectric or other devices. This electrical energy is applied to circuitry, which produces a desired stimulating pulse waveform, which is then applied to tissue-contacting electrodes.

In a manner similar to the wireless acoustic pacemaker, the wireless acoustic implantable defibrillator described herein also comprises a subcutaneously implanted controller-transmitter operating in conjunction with a receiver-defibrillator (similar to the receiver-stimulator of the wireless acoustic pacemaker) device located within the chambers of the heart. These components of the defibrillator and their pacemaker counterparts have significant differences, because of the differences in energy requirements and applied electrical waveform of a defibrillator versus a pacemaker, and in the frequency of application of this energy. In a defibrillator, the acoustic transmitter must transmit a much larger amount of energy to effect defibrillation, either through increased acoustic amplitude, increased transmission time, or both. However, a defibrillator device may only need to apply this energy a small number of times over the lifetime of the device. Both of these requirements are in contrast to a bradycardia pacemaker, which must supply a very small amount of energy, typically at the rate of 60-80 times per minute, continuously for a period of many years. Even anti-tachycardia pacing, which is typically delivered at a rate of 150-200 beats per minute, is only performed typically a few times per year.

In this invention, the acoustic transmitter is adapted to analyze the electrogram to detect specific arrhythmias, including ventricular tachycardia and ventricular or atrial fibrillation. When such a condition is detected, a suitable acoustic transmission (either antitachycardia pacing or defibrillation) is initiated and directed towards the implanted receiver-defibrillator.

The implanted receiver-defibrillator is significantly larger than a corresponding pacemaker receiver-stimulator, extending from the apex of the right ventricle into the right atrium, and then upwards into the superior vena cava brachiocephalic vein, subclavian vein, or other suitable vein generally superior to the heart. The purpose of this length is to provide a greater area with which to receive the transmitted acoustic energy, to allow sufficient separation between the desirable locations for the defibrillation electrodes, and to house additional energy storage components and waveform shaping circuitry. When the receiver-defibrillator intercepts acoustic energy from the transmitter, the acoustic energy is converted to electrical energy by piezoelectric or other transducers. This energy is rectified and stored, typically in one or more capacitors. When sufficient energy has been stored, waveform shaping circuitry applies the defibrillation pulse between electrodes located at the ends of the receiver device, thus applying the defibrillation energy to the heart.

Additionally, wireless acoustic receiver-defibrillator and receiver-stimulator (pacemaker, as described in co-pending applications) functions will preferably be combined in a single device.

DETAILED DESCRIPTION OF THE INVENTION

The invention described here comprises a subcutaneously implanted controller-transmitter device that transmits acoustic energy to an implanted receiver-defibrillator device, which converts the acoustic energy to electrical energy, stores and accumulates a sufficient quantity of energy, and then discharges such energy in a preferred waveform between at least two electrodes disposed on or about the receiver-defibrillator device in order to terminate an undesirable cardiac rhythm. The acoustic energy can be delivered as single or multiple bursts, preferably using ultrasound. The ultrasound frequency may range from 20 kHz to 10 MHz, preferably 100 kHz to 1 MHz, and more preferably from 250 to 500 kHz. The ultrasound transmit burst length (or accumulated burst length in the event of multiple bursts) will be less than 10 seconds, preferably less than 5 seconds, and more preferably less than 2 seconds.

The controller-transmitter device comprises one or more ultrasound transducers of appropriate size(s) and aperture(s) to generate sufficient acoustic energy to achieve the desired efficient transfer of energy to the implanted receiver-defibrillator device.

The controller-transmitter device containing the transmitting transducer is implanted typically just beneath the skin in the subcutaneous space, and can also be positioned beneath the pectoral muscles.

The controller-transmitter device comprises sensors, such as electrodes for detecting the patient's electrocardiogram (ECG). Such electrodes or other sensors are preferably disposed on or incorporated into or within the housing or on appendage of the controller-transmitter device. Circuitry and algorithms utilizing these signals to detect potentially dangerous arrhythmias and to control the delivery of ultrasound energy are also incorporated in the controller-transmitter device.

The receiver-defibrillator device is typically located in the right ventricle of the heart and preferably in the apex of the right ventricle. Fixation of the device to the heart muscle is accomplished by means of a helical screw, barbs, tines, or the like, in similar fashion to currently available active fixation pacemaker/defibrillator lead wires, and as described in co-pending applications. The elongated body of the device extends into the right atrium through the tricuspid valve, and into the superior vena cava, and possibly continuing into one of the brachiocephalic or subclavian veins. One of the defibrillation electrodes is disposed on the outer surface, near the distal end of the receiver-defibrillator body, preferably near the apex of the right ventricle. The second defibrillation electrode is disposed on the proximal end of the device, and is located within the superior vena cava, brachiocephalic or left subclavian vein. The receiver-defibrillator will contain multiple acoustic receiving transducers within its body, preferably disposed towards the distal end within the right ventricle. The proximal portion of the device may contain circuitry and devices to accomplish energy conversion and storage, and waveform shaping as described below.

The wireless acoustic defibrillator system will preferably also incorporate cardiac stimulation (pacemaker) functions by being combined with wireless acoustic pacemaker technology as described in the co-pending applications. Cardiac stimulation would be applied for example as backup pacing following defibrillation treatment, as anti-tachycardia pacing, as pacing for bradycardia, conduction blocks, heart failure, and other conditions. Incorporation of pacing with the capability to defibrillate is similar to existing ICD devices. In the wireless pacemaker-defibrillator system of the present invention, additional stimulation electrodes would be disposed on the distal tip of the receiver-defibrillator device where they would be in contact with the right ventricle for the purpose of pacing the right ventricle, and/or disposed on the surface of or otherwise connected to the receiver-defibrillator device in the right atrium for the purpose of pacing the right atrium. If it is desired to provide left ventricular stimulation as well, in order to provide the function of a CRT-D (cardiac resynchronization therapy-defibrillation) device, an additional wireless receiver-stimulator, as described above and in more detail in the co-pending applications, would be implanted into the left ventricle.

Different embodiments of wireless acoustically-powered cardiac defibrillator and defibrillator/pacemaker systems according to the present invention are illustrated in FIGS. 1 through 6.

Figure 1A:
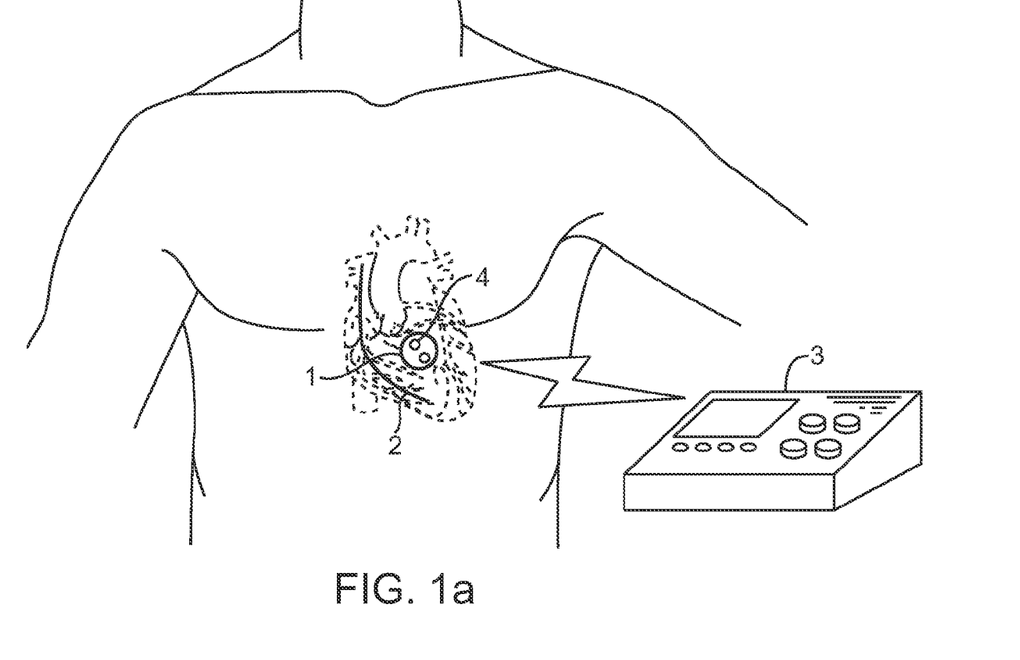
FIGS. 1a and 1b are schematics showing the acoustic-powered wireless defibrillator system in application with an implanted transmitter-controller.

FIG. 1 illustrates a basic configuration for an implantable wireless acoustic defibrillator. In FIG. 1a, a controller-transmitter device 1 containing circuitry to provide arrhythmia detection and ultrasound transmission is implanted beneath the skin, and generally over the heart. Upon detection of an arrhythmia that requires treatment, acoustic energy is transmitted by this device through intervening tissue to the receiver-defibrillator device 2 which is affixed within the heart, extending from the apex of the right ventricle through the right atrium and into the superior vena cava or further into one of the brachiocephalic or subclavian veins. The receiver-defibrillator device 2 contains means to receive this acoustic energy and convert it into an electrical defibrillating pulse, which is then applied to electrodes incorporated into the body of the device. The controller-transmitter 1 incorporates sensing electrodes 4 and circuits and algorithms (not shown) that use the electrogram (ECG) to detect potentially dangerous arrhythmias. These sensing electrodes may be disposed on the outer surface of the controller-transmitter or may be adapted to extend from the controller-transmitter, for example by lead wires, to improve the sensing capability of the device. Based on the output of the sensing electrodes, the control circuitry initiates the acoustic transmission, which will result in defibrillation. Additionally, the controller-transmitter device comprises means to communicate with an outside programmer 3 to allow setting up of system parameters, monitoring of performance, and other such functions.

Figure 1B:
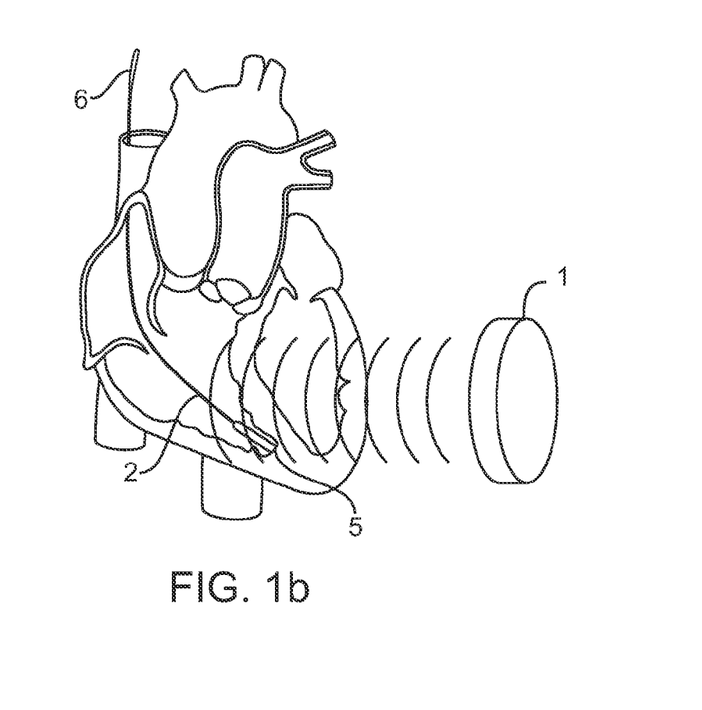

FIG. 1b is a cross-sectional view of the heart in the previous example, showing the receiver-defibrillator device 2 implanted in the heart with a distal end affixed to the right ventricular apex. Acoustic energy is transmitted from the subcutaneously implanted controller-transmitter 1 in the direction of the receiver-defibrillator 2. The body of the receiver-defibrillator device contains acoustic transducers to receive the acoustic energy and convert it into electrical energy, and circuitry which stores the electrical energy and generates a desired waveform which is applied to electrodes to terminate the arrhythmia. The receiver-defibrillator incorporates a distal electrode 5 at or near the right ventricular apex, and a proximal electrode 6 which would be located typically in the superior vena cava or other vein generally above the heart.

Figure 2:
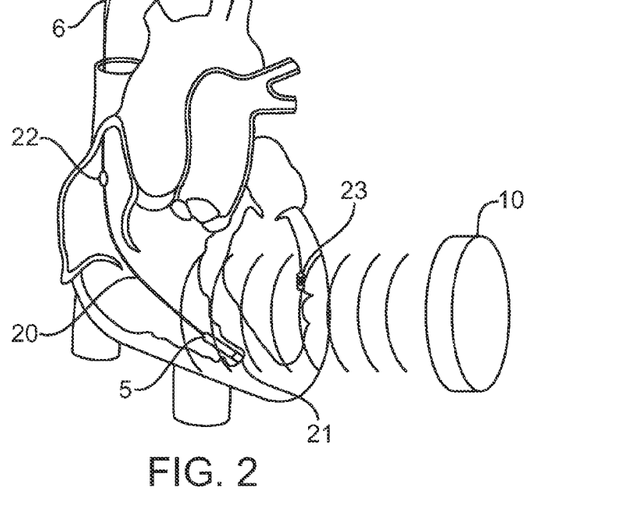
FIG. 2 is a schematic showing the acoustic-powered wireless defibrillator system in application with a co-implanted receiver-stimulator.

FIG. 2 depicts a configuration of the present invention including pacemaker functions. In addition to the functions described above, the controller-transmitter 10 contains circuitry and algorithms common to currently available pacemaker devices, which would typically include timing circuitry, an ECG sensing system possibly comprised of sensing electrodes, motion detectors, and other types of physiologic sensors to assist in determining pacing rates, and signal conditioning and analysis functions for the various electrodes and detectors. The receiver-defibrillator-stimulator device 20 contains a right ventricular stimulation (pacing) electrode 21 in contact with right ventricular tissue in addition to distal defibrillation electrode 5, proximal defibrillation electrode 6, and, optionally, a right atrial stimulation electrode 22 in contact with right atrial tissue. The right atrial stimulation electrode 22 may be incorporated onto the body of receiver-defibrillator-stimulator device 20 as shown, or may be disposed onto an appendage extending from the main body of receiver-defibrillator-stimulator device 20 and positioned to maintain contact with the atrial wall. The controller-transmitter 10 and receiver-defibrillator-stimulator 20 would comprise the functional equivalent of a current ICD system having single or optionally dual-chamber pacing capabilities. An independent implantable receiver-stimulator 23 may also placed in the left ventricle, adding bi-ventricular pacing function, thus providing the functional equivalent of a current CRT-D system. The implantable receiver-stimulator 23 is of the type described in co-pending applications previously cited. Briefly, the receiver-stimulator intercepts at least a portion of the transmitted acoustic energy, and converts that acoustic energy into electrical energy using piezoelectric or other devices. This electrical energy is applied to circuitry, which produces a desired stimulating pulse waveform, which is then applied to tissue-contacting electrodes, which in turn provides the desired pacing effect.

Figure 3:
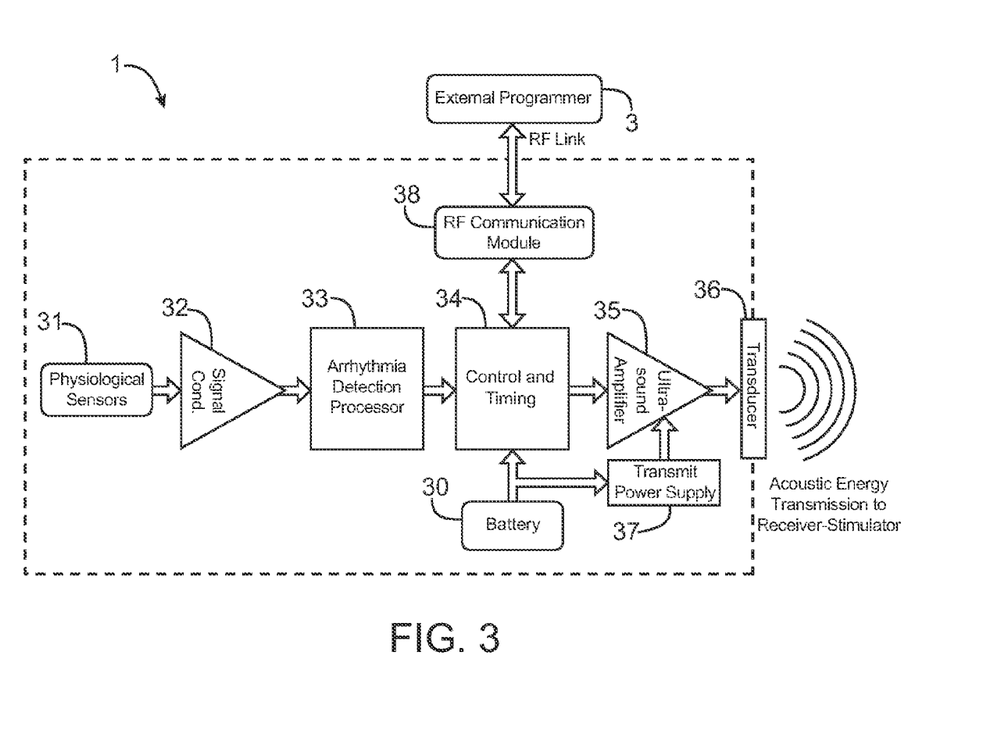
FIG. 3 is a block diagram showing components of the acoustic controller-transmitter of the present invention.

A block diagram of the controller-transmitter component of an acoustically powered wireless defibrillator is shown in FIG. 3. The controller-transmitter device 1 comprises a battery 30, which is optionally a rechargeable battery; multiple electrodes and possibly other sensors 31 which may or may not be in direct contact with tissue to detect the patient's electrocardiogram, these being connected to signal conditioning circuitry 32; an arrhythmia detection processor 33; a control and timing module 34 which may store operational parameters and which receives arrhythmia information from the arrhythmia detection processor and uses this information to generate the required control signals to activate the ultrasound transmit amplifier 35 which drives one or more transmitting ultrasound transducers 36 producing the desired acoustic beam. A transmit power supply 37, typically a DC-DC converter, provides a voltage characteristically higher than the voltage of battery 30, which is used by the ultrasound transmit amplifier 35. A communications module 38 whose function is to provide a data path, for example by RF communication to and from an external unit 3, allows the physician to set device parameters and to acquire diagnostic information about the patient and/or the device.

Figure 4A:
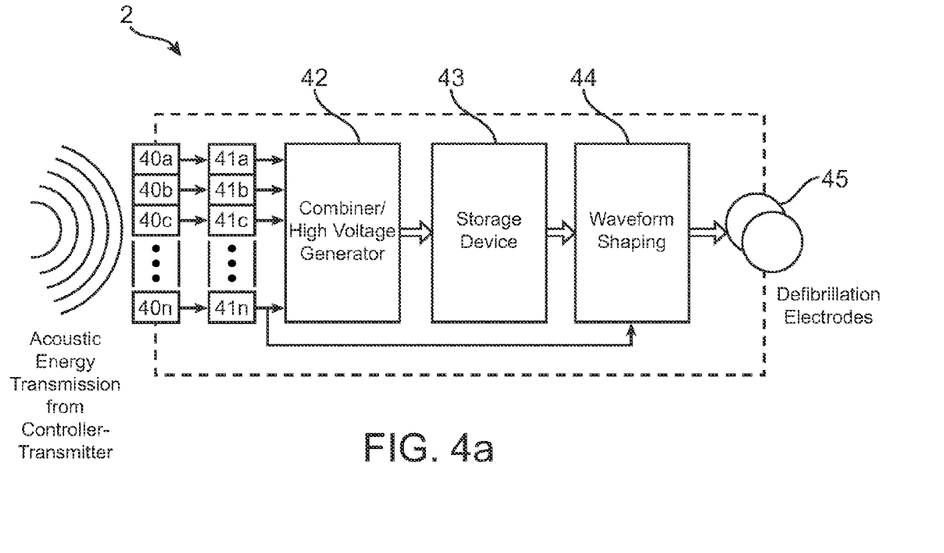
FIGS. 4a and 4b are block diagrams showing the components of the acoustic receiver-defibrillator of the present invention.
Figure 4B:
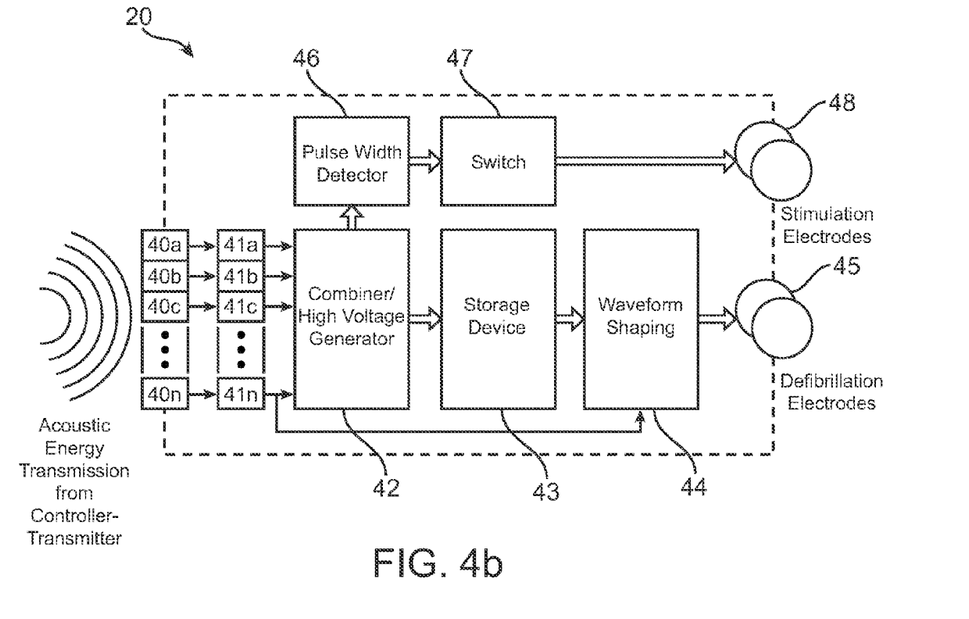

FIG. 4 depicts block diagrams of implantable receiver-defibrillator (FIG. 4a) and receiver-defibrillator-stimulator devices (FIG. 4b). In FIG. 4a, receiver-defibrillator device 2 is shown. The device contains multiple receiving ultrasound transducers 40a to 40n which intercept at least a portion of the acoustic energy transmitted from controller-transmitter 1. Each receiving transducer produces an alternating electrical signal representing the alternating nature of the transmitted ultrasound pressure wave. The electrical signals from the individual receiving transducers are applied to separate electrical circuits 41a-41n, which in accordance with co-pending applications previously cited, results in an isotropic receiver, insensitive to the orientation of the receiving elements with respect to the transmitted acoustic beam. Each circuit 41a-41n may contain one or more circuit elements of a type commonly known as a rectifier or detector, which produces a DC voltage, and which may have one of many known circuit configurations. The individual outputs from the circuits 41a-41n are fed to a circuit 42 to produce a DC voltage. Circuit 42 may contain high voltage generation circuitry, typically DC-to-DC converter circuitry having one of many known circuit configurations, to boost the voltage to a desired level. The DC voltage so produced is stored in energy storage element 43, which may typically be a capacitor. This storage element may be disposed at a variety of positions (not shown) on the receiver-defibrillator within the heart or outside the heart within the vascular access, for example at a proximal location, at a distal location, anywhere along the length of the device, or as an appendage of the device. A small portion of the received energy is used to provide power to waveform shaping circuitry 44 which produces a defibrillation waveform of a desired shape and duration. This defibrillation waveform is applied to electrodes 45 which may be incorporated onto the outer surface of the device. The defibrillation waveform is applied when the waveform shaping circuitry senses that sufficient energy is contained in the storage device to accomplish defibrillation, which may be a predetermined amount of energy, or automatically when the waveform shaping circuit detects the end of the ultrasound transmission from the controller-transmitter, or as a result of detecting a command from the controller-transmitter which may be encoded into the ultrasound transmission by one of various commonly known modulation schemes.

FIG. 4b presents a modification to the block diagram of FIG. 4a, with additional circuitry for an implantable receiver-defibrillator-stimulator device 20. As well as including all of the functional elements previously described for the receiver-defibrillator device 2, following the rectifier-detector circuits 41a-41n in this device is a pulse width detector 46 and switch 47 which allow energy from a short acoustic transmission, typically less than 2.0 milliseconds in duration and preferably 0.5 msec, which would correspond to a typical pacing stimulus duration, to pass through unimpeded to one or more pairs of stimulation electrodes 48. An acoustic transmission lasting longer than a given time, for example longer than 2 msec, would cause the pulse width discriminator 46 to open switch 47, disconnecting the stimulation electrodes 48 and diverting the received energy solely to the defibrillation circuitry.

FIG. 5 is a simplified representation of the acoustic and electrical signals of the wireless acoustic ICD shown in FIGS. 1 through 4. FIG. 5a depicts the transmitted acoustic signal 51 generated by the controller-transmitter device 1 in response to the detection of an arrhythmia requiring defibrillation. The acoustic signal is characterized by its oscillation frequency $F=1/t$ (t being the period of the acoustic waveform), an acoustic pressure amplitude indicated by the maximum positive pressure $+P_{max}$ and maximum negative pressure $-P_{max}$, and a burst duration T. The burst duration T may be of a predetermined, fixed length, or may be variable, continuing until the defibrillation pulse is applied by the receiver-defibrillator, which is in turn detected by the controller-transmitter, or until the undesired arrhythmia is successfully terminated after one or more defibrillation shocks, which may also be detected by the controller-transmitter. The acoustic pressure wave, when striking the receiving transducer elements 40a-40n in the receiver-defibrillator device 2 generates in each transducer element an electrical signal 52 as shown in FIG. 5b, having frequency matching that of the transmitted acoustic waveform 51 and an amplitude proportional to the transmitted acoustic pressure ($\sim +/-P_{max}$) indicated by the maximum positive voltage $+V_{max}$ and maximum negative voltage $-V_{max}$. The proportionality factor may vary from element to element due to manufacturing differences, differences in distance and relative orientation between the transmitter and individual receiver elements, non-uniformity of the transmitted acoustic beam, attenuation of the acoustic energy by body structures, and other factors.

Figure 5A:
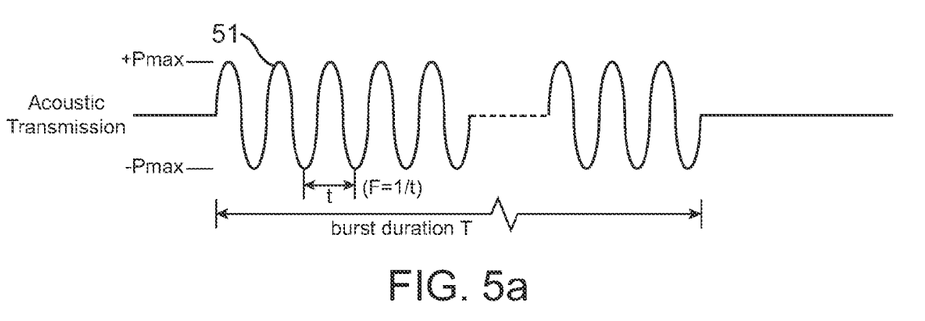
FIG. 5a-5e illustrate representative acoustic and electrical signals useful in the systems and methods of the present invention.
Figure 5B:
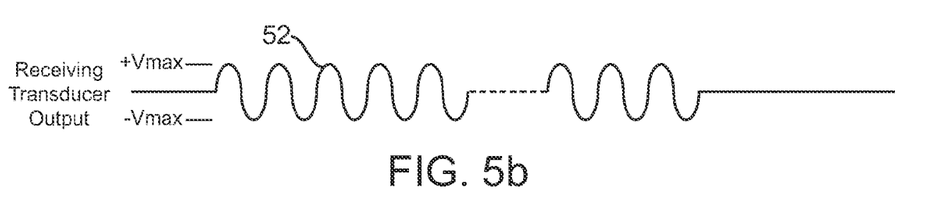
Figure 5C:
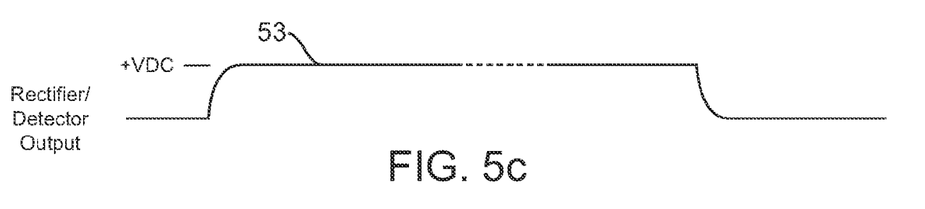
Figure 5D:
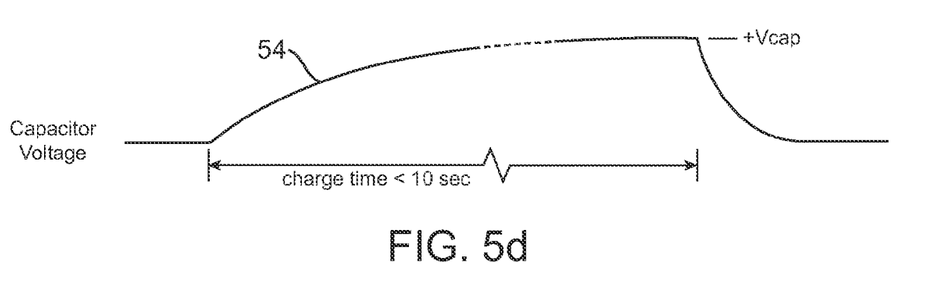
Figure 5E:
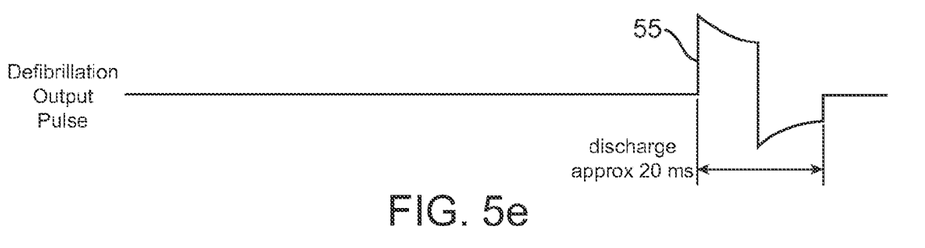

FIG. 5c shows the waveform 53 resulting from rectification and filtering of waveform 52 by circuits 41a-41n, which produce a DC signal having magnitude $+V_{DC}$ proportional to the amplitude of the receiving transducer waveform 52. The individual contributions from each transducer element 40a-40n and rectifier-detectors 41a-41n are combined in series, or in parallel, or in a combination thereof and converted to a higher voltage by circuitry 42, which is used to charge the energy storage component 43, which is typically a capacitor. FIG. 5d represents a typical voltage waveform 54, which is that of a capacitor during both charging and discharging phases. When the desired energy storage level is attained, or when triggered by cessation of the ultrasound transmission or detection of a command encoded within the transmitted ultrasound, or through other means, waveform shaping circuitry 44 initiates the discharge of the energy storage component 43, creating a waveform 55 as shown in FIG. 5e, having a desired shape to accomplish defibrillation, which may include the typically 5-10 msec duration biphasic waveform shown which is provided by most implantable defibrillator devices.

Figure 6:
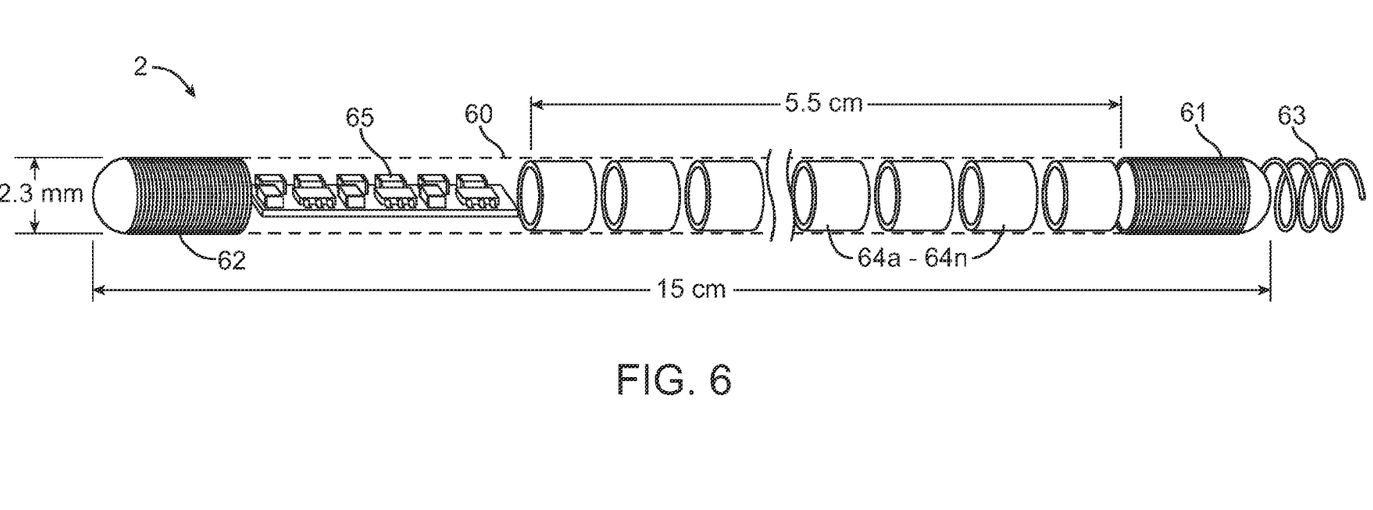
FIG. 6 is a schematic illustration showing an embodiment of the receiver-defibrillator device of the present invention.

FIG. 6 depicts a cross-sectional view of one embodiment of an implantable receiver-defibrillator device 2. The device in general has an elongated cylindrical shape, with a diameter of preferably 2 to 3 mm and an overall length of preferably 15 to 20 cm. Flexibility of the device is maintained by a soft outer sheath 60 typically made of nylon, silicone rubber, polyurethane, PTFE, or other suitable material, which also serves to protect and electrically insulate the internal devices and circuits. Distal and proximal defibrillation electrodes 61 and 62, respectively, are also of flexible design, possibly coiled metal, as used in most ICD lead systems currently available. A helical coil type device 63 for fixation of the distal end into the right ventricular apex is shown; other traditional fixation methods such as the use of barbs, tines, and the like could also be used. The helical coil 63 may also function as a ventricular stimulation electrode if device 2 is implemented as a receiver-stimulator-defibrillator device. A number of receiving transducers 64a-64n are disposed internal to the sheath, near the distal end of the device. In accordance with co-pending applications previously cited, the individual transducers are cylindrical devices having both a length and diameter less than or equal to ½ wavelength of the transmitted acoustic signal in order to ensure high isotropic reception patterns regardless of the relative orientation between the transmitting and receiving transducers. As an example, at one preferred acoustic frequency of 340 kHz, the receiving transducer elements should be less than or equal to 2.25 mm in any dimension. To maintain flexibility of the device, a flexible spacing between individual transducer elements is provided. As one possible example, with the above dimensions and 0.5 mm spacing between elements, 20 elements would be disposed along approximately 5.5 cm of device length. Wires (not shown) connect the individual transducer elements 64 with circuitry and energy storage elements 65, containing individual circuit elements as previously described. Preferably the circuitry 65 would be provided on a flexible substrate, a common manufacturing process. Additional wires, also not shown, connect the circuitry 65 to the electrodes 61 and 62.

In any ICD device, the elapsed time between the detection of the arrhythmia and the actual discharge of the defibrillation energy is a critical parameter. In a conventional ICD as well as in this invention, a capacitor must first be charged to a high voltage sufficient to effect defibrillation of the heart, typically 400-600 volts. In terms of energy, the defibrillation threshold (ICD discharge energy) for most patients ranges from 6 to 25 Joules, with average defibrillation thresholds being in the range of 10-15 J. In a conventional ICD, the energy from a low-voltage battery, typically 2-3 VDC, which also typically has a limited current capability, must be used to charge a capacitor to a high voltage, typically requiring a DC-DC converter. This process takes 5-10 seconds in most currently available ICD devices. To estimate the charge-time latency for the acoustically-powered wireless ICD, data from prototype single crystal receiver transducer elements and rectifier/detector circuits, as disclosed in co-pending applications, can be utilized. Current transducer devices for implantable receiver-stimulator (pacemaker) applications, having diameter and length dimensions of 1.78 mm, have been demonstrated to produce 14.30 Volts into a 500Ω load after rectification and detection, with an applied acoustic rarefactional pressure of 1.0 mega Pascal (MPa). Such a device would then produce 0.409 Watts per applied mega Pascal. In terms of energy, each transducer element would thus produce 0.409 Joules per second. A receiver-defibrillator device comprising at least 20 such transducer elements would then produce 8.18 J/sec. Therefore, the charge time to accumulate 20 J would be 2.45 seconds. Even limiting this charge time by assuming a reasonable overall efficiency of the electronics (DC-DC converter, etc.) of 85%, 20 elements would then produce a usable 6.95 J/s giving a charge time of under 3 seconds. This compares favorably with all currently available ICD devices. It is interesting to note that at one preferred ultrasound frequency of 380 kHz, an acoustic field having a peak rarefactional pressure of 1.0 MPa produces a mechanical index (MI) of 1.62 (MI=P/$\sqrt{\text{Frequency}}$ where P is the peak rarefactional pressure in MPa, and frequency is in MHz), which is less than the FDA mandated limit of 1.9 MI for diagnostic ultrasound imaging. Assuming that in the event of a life-threatening arrhythmia such as ventricular tachycardia or fibrillation a higher MI will be permitted, it can be seen that the charge time which exists between detection of the arrhythmia and possible application of the defibrillation shock can be greatly reduced as compared to currently available ICDs. As one example, increasing the acoustic peak rarefactional pressure to 2.0 MPa (3.24 MI at 380 kHz) would result in a charge time that is less than 1.5 seconds.

In another embodiment of this invention, the controller-transmitter device 1 is programmed to fully charge the storage device 43 of receiver-defibrillator 2 or 20 at a slower rate over a relatively longer period (charge times on the order of 1 minute would be acceptable) following implant and activation. Receiver-defibrillator 2 or 20 would not immediately deliver a defibrillation shock, but would incorporate switching electronics (not shown) within waveform shaping circuitry 44 to isolate the storage device and maintain its state of charge. Upon detection of an arrhythmia requiring defibrillation, a signal encoded into an ultrasound transmission from the controller-transmitter would be detected by the receiver-defibrillator causing it to apply the defibrillation shock. Because there is unavoidable leakage of charge over time due to capacitor leakage, non-infinite switch impedance, and the like, it would be necessary for the controller-transmitter to periodically provide a small recharge pulse to maintain the fully charged state of the storage device. In the case of the combined receiver-defibrillator-stimulator device 20 a small portion of the periodic energy supplied at each stimulation pulse could be used for this purpose. Having a continually charged receiver-defibrillator would provide the ability to deliver, with essentially no delay after detection of an arrhythmia, a defibrillation shock. This is a significant advantage over current ICD designs which typically require 5-10 seconds to deliver treatment.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A method for treating cardiac fibrillation or cardiac tachycardia, said method comprising:
    implanting a controller-transmitter at a subcutaneous implantation site to generate acoustic energy, wherein the controller-transmitter comprises sensing electrodes that are configured to detect undesirable cardiac arrhythmias;
    implanting a receiver-defibrillator at a cardiac implantation site, wherein the receiver-defibrillator comprises one or more electrode assemblies adapted to deliver defibrillation energy to cardiac tissue;
    generating acoustic energy at the subcutaneous implantation site using the controller-transmitter;
    receiving said acoustic energy at the cardiac implantation site using the receiver-defibrillator; and
    using an external programmer to program one or more settings of the controller-transmitter;
    wherein said acoustic energy is converted to electrical energy by the receiver-defibrillator at a rate of 1-10 J/sec, stored at a level to produce appropriate amplitude, and delivered with an appropriate waveform sufficient to treat the cardiac fibrillation or cardiac tachycardia.

2. A system for treating cardiac fibrillation or cardiac tachycardia, said system comprising:
    an implantable acoustic controller-transmitter comprising sensing electrodes configured to detect undesirable cardiac arrhythmias; and
    an implantable acoustic receiver-defibrillator having electrode assemblies adapted to deliver defibrillation energy to the cardiac muscle tissue; and
    an external programmer configured to program one or more settings of the controller-transmitter;
    wherein the controller-transmitter and receiver-defibrillator are adapted to transmit and receive acoustic energy, respectively, which provides both defibrillation energy and signal information to the receiver-defibrillator sufficient to provide cardiac defibrillation or termination of cardiac tachycardia, and wherein the receiver-defibrillator is configured to convert the received acoustic energy to electrical energy at a rate of 1-10 J/sec.

3. The system as in claim 2, wherein the receiver-defibrillator comprises an acoustic receiver which receives acoustic energy and converts the acoustic energy to electrical energy, means for accumulating and storing the electrical energy, means to generate an appropriate waveform from the stored electrical energy to defibrillate the cardiac tissue, and defibrillation electrodes adapted to deliver the defibrillation waveform to cardiac tissue.

4. The system of claim 3, wherein the receiver-defibrillator has distal and proximal ends, where the distal end of the receiver-defibrillator is adapted to be secured in the right ventricular apex of the heart, and the proximal end is adapted to be located above the heart.

5. The system of claim 4, wherein one defibrillation electrode is adapted to be located near the right ventricular apex of the heart, another defibrillation electrode is adapted to be located within brachiocephalic, subclavian, or a vein generally superior to the heart.

6. The system of claim 3, wherein the controller-transmitter comprises a power source, control and timing circuitry to detect undesirable cardiac arrhythmias and provide a defibrillation output signal, means for converting the defibrillation output signal to an acoustic energy signal, and means for transmitting the acoustic energy signal to the receiver-defibrillator.

7. The system of claim 6, wherein the control circuitry is configured to process an ECG signal from the sensing electrodes, and wherein the sensing electrodes are adapted to be located on the exterior surface of the controller-transmitter and in contact with body tissue.

8. A method for treating cardiac fibrillation or cardiac tachycardia and stimulating cardiac muscle, said method comprising:
    implanting a controller-transmitter at a subcutaneous implantation site to generate acoustic energy, wherein the controller-transmitter comprises sensing electrodes that are configured to detect undesirable cardiac arrhythmias;
    implanting a receiver-defibrillator-stimulator at a cardiac implantation site, wherein the receiver-defibrillator-stimulator comprises one or more electrode assemblies adapted to be in direct contact with cardiac tissue and deliver defibrillation or stimulation energy to cardiac muscle tissue;
    generating acoustic energy at the subcutaneous implantation site using the controller-transmitter; and
    receiving said acoustic energy at the cardiac implantation site using the receiver-defibrillator-stimulator; and
    using an external programmer to program one or more settings of the controller-transmitter;
    wherein said acoustic energy is converted by the receiver-defibrillator-stimulator to electrical energy at a rate of 1-10 J/sec, wherein the electrical energy is suitable for either cardiac defibrillation or for treating cardiac tachycardia or for cardiac muscle stimulation based on both energy and signal information encoded in the generated acoustic energy.

9. The method of claim 8, wherein receiving stimulating energy comprises receiving the acoustic energy at least two different cardiac sites.

10. The method of claim 8, wherein a predetermined configuration causes stimulation of at least two different sites simultaneously.

11. A system for treating cardiac fibrillation or cardiac tachycardia and for stimulating cardiac muscle tissue, said system comprising:
    an implantable acoustic controller-transmitter comprising sensing electrodes configured to detect cardiac arrhythmias; and
    an implantable acoustic receiver-defibrillator-stimulator having electrode assemblies adapted to deliver defibrillation energy or stimulation energy to the cardiac muscle tissue; and
    an external programmer configured to program one or more settings of the controller-transmitter;
    wherein the controller-transmitter and receiver-defibrillator-stimulator are adapted to transmit and receive acoustic energy, respectively, which provides energy to the receiver-defibrillator-stimulator sufficient for accomplishing one of either stimulation or defibrillation, and which also provides signal information sufficient to perform cardiac defibrillation or termination or cardiac tachycardia, and wherein the receiver-defibrillator-stimulator is configured to convert the received acoustic energy to electrical energy at a rate of 1-10 J/sec.

12. The system of claim 11, wherein the receiver-defibrillator-stimulator has proximal and distal ends, and wherein the receiver-defibrillator-stimulator comprises an acoustic receiver which receives acoustic energy and generates an alternating current signal, means for converting the alternating current signal to a direct current signal and further converting the direct current signal into stimulation energy or defibrillation energy, means for detecting whether the acoustic energy is intended to stimulate or defibrillate, means for applying stimulation energy to stimulation electrodes adapted to deliver the stimulation energy to myocardial tissue, means for accumulating and storing defibrillation energy, means to generate an appropriate waveform to defibrillate the cardiac tissue utilizing the stored defibrillation energy, and defibrillation electrodes adapted to deliver the defibrillation waveform to myocardial tissue.

13. The system of claim 12, wherein the distal end of the receiver-defibrillator-stimulator is adapted to be secured in the right ventricular apex of the heart, and wherein the proximal end is adapted to be located above the heart in the superior vena cava.

14. The system of claim 12, wherein the distal end of the receiver-defibrillator-stimulator is adapted to be secured in the right ventricular apex of the heart, and wherein the proximal end is adapted to be located above the heart.

15. The system of claim 12, wherein one defibrillation electrode is adapted to be located near the right ventricular apex of the heart, a second defibrillation electrode is adapted to be located within the superior vena cava, brachiocephalic vein or left subclavian vein, and one stimulation electrode is adapted to be located near the right ventricular apex of the heart in contact with right ventricular tissue.

16. The system of claim 15, wherein a second stimulation electrode is adapted to be located within the right atrium of the heart and disposed on the surface of the receiver-defibrillator-stimulator in such a manner to be in contact with right atrial tissue.

17. The system of claim 15, wherein a second stimulation electrode is adapted to be located within the right atrium of the heart and connected to the receiver-defibrillator-stimulator in such a manner to be in contact with right atrial tissue.

18. The system of claim 15, wherein a second stimulation electrode is adapted to provide stimulation to the right atrium sequentially with respect to the stimulation of the right ventricle.

19. The system of any one of the claims 11 through 18, wherein at least one independent receiver-stimulator is adapted to be secured within the left ventricle and provide stimulation synchronous with the stimulation of the right ventricle.

20. The system of any one of the claims 11 through 18, wherein at least one independent receiver-stimulator is adapted to be secured within the left ventricle and provide stimulation sequentially with the stimulation of the right ventricle.

21. The system of claim 11, wherein the controller-transmitter comprises a power source, control circuitry and timing circuitry to provide a pacing signal and to detect undesirable cardiac arrhythmias and provide a pacing or defibrillating output signal, means for converting the output signal to an acoustic energy signal, and means for transmitting the acoustic energy signal to the receiver-defibrillator-stimulator.

22. The system of claim 21, wherein control circuitry includes the sensing electrodes in order to adjust timing of stimulation or to detect undesirable cardiac arrhythmias.

23. The system of claim 22, wherein one or more physiologic variables sensed by the sensing electrodes determine the appropriate pacing or defibrillation therapy.

24. The system of claim 22 or 23, wherein the control circuitry is configured to process an ECG signal from the sensing electrodes, and wherein the sensing electrodes are located on the exterior surface of the controller-transmitter and adapted to be in contact with body tissue.

25. The system of claim 11, wherein the controller-transmitter comprises a housing and the sensing electrodes are disposed on the housing.

26. The system of claim 25, wherein the sensors are directly connected to the signal processing circuitry of the controller-transmitter.

27. The system of claim 11, wherein the external programmer transmits a radiofrequency signal and the controller-transmitter comprises circuitry for receiving the radiofrequency signal.

28. The system of claim 11, wherein the receiver-defibrillator-stimulator comprises ultrasound transducers, which convert acoustic energy to electrical energy, and the receiver-defibrillator-stimulator stores the converted electrical energy in response to the acoustic energy transmitted by the controller-transmitter, circuitry which detects a stimulation signal from the controller-transmitter, and at least one electrode which delivers the electrical energy to the electrode assemblies.

29. The system of claim 11, wherein the electrode assemblies are spaced further apart than conventional pacing electrodes.

* * * * *